US009235973B2

(12) United States Patent
Popescu

(10) Patent No.: US 9,235,973 B2
(45) Date of Patent: Jan. 12, 2016

(54) METHOD AND MEDICAL IMAGING DEVICE FOR COMMUNICATION BETWEEN A CONTROL UNIT AND A PATIENT AND/OR AN OPERATOR

(71) Applicant: Stefan Popescu, Erlangen (DE)

(72) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 153 days.

(21) Appl. No.: 13/927,347

(22) Filed: Jun. 26, 2013

(65) Prior Publication Data

US 2013/0342350 A1 Dec. 26, 2013

(30) Foreign Application Priority Data

Jun. 26, 2012 (DE) .......................... 10 2012 210 821

(51) Int. Cl.
| | |
|---|---|
| *A61M 21/00* | (2006.01) |
| *A61B 5/05* | (2006.01) |
| *G08B 1/08* | (2006.01) |
| *G08B 21/02* | (2006.01) |
| *A61B 6/00* | (2006.01) |
| *A61B 5/00* | (2006.01) |
| *A61B 5/055* | (2006.01) |

(52) U.S. Cl.
CPC ............... *G08B 21/02* (2013.01); *A61B 5/002* (2013.01); *A61B 5/0555* (2013.01); *A61B 6/461* (2013.01); *A61B 6/467* (2013.01); *A61M 21/00* (2013.01); *A61M 2021/005* (2013.01); *A61M 2021/0027* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,562,464 | A * | 12/1985 | Kurihara | H04N 5/32 348/E5.086 |
| 6,175,610 | B1 * | 1/2001 | Peter | 378/8 |
| 7,308,075 | B2 * | 12/2007 | Barkow et al. | 378/20 |
| 2004/0193413 | A1 * | 9/2004 | Wilson et al. | 704/243 |
| 2004/0254840 | A1 * | 12/2004 | Slemmer | G06Q 10/02 705/22 |

(Continued)

FOREIGN PATENT DOCUMENTS

DE 10 2008 033 158 A1 1/2010

OTHER PUBLICATIONS

Ni et al., AnatOnMe: Facilitating Doctor-Patient Communication Using a Projection-Based Handheld Device, Proceedings of ACM CHI 2011 (2011).

(Continued)

*Primary Examiner* — Fekadeselassie Girma
(74) *Attorney, Agent, or Firm* — Schiff Hardin LLP

(57) ABSTRACT

In a method and apparatus for communication between a control unit of a medical imaging device, the control unit being arranged within a control room, and an operator located in an examination room examination and/or a patient located in the examination room and positioned on a patient support device, wherein the control room is arranged outside of the examination room, object data of objects positioned on the patient support device and/or of the operator are acquired by an object data acquisition unit, the acquired object data are transferred from the object data acquisition unit to the control unit, information of the objects positioned on the patient support device and/or the operator is determined by the control unit using the acquired object data, and output information is generated using the determined information and the output information is presented within the examination room.

37 Claims, 5 Drawing Sheets

(56) References Cited

U.S. PATENT DOCUMENTS

| | | | |
|---|---|---|---|
| 2005/0283068 A1* | 12/2005 | Zuccolotto et al. | 600/410 |
| 2006/0193437 A1 | 8/2006 | Boeing et al. | |
| 2007/0172102 A1 | 7/2007 | Hempel | |
| 2007/0185739 A1* | 8/2007 | Ober | G06Q 50/24 705/3 |
| 2011/0137680 A1* | 6/2011 | Sweeney | G06F 19/327 705/3 |
| 2011/0140922 A1* | 6/2011 | Levy | G01C 21/3685 340/932.2 |
| 2013/0022257 A1* | 1/2013 | Omernick | G06F 19/3406 382/132 |
| 2013/0064346 A1* | 3/2013 | Ferren | G01N 23/04 378/62 |
| 2013/0215235 A1* | 8/2013 | Russell | 348/47 |
| 2013/0295539 A1* | 11/2013 | Wilson et al. | 434/247 |
| 2014/0048730 A1* | 2/2014 | Niedzielski | A61B 6/107 250/519.1 |
| 2014/0088405 A1* | 3/2014 | Assmann | A61B 5/0531 600/411 |
| 2014/0358002 A1* | 12/2014 | Daoura | 600/443 |

OTHER PUBLICATIONS

Harrison et al., OmniTouch: Wearable Multitouch Interaction Everywhere, ACM UIST'11 (2011).

/research.microsoft.com/en-us/um/redmond/groups/cue/anatonme (2011).

Wikipedia: "KINECT," Microsoft's motion sensing input device (2010).

Wikipedia: "Speech Recognition".

Wikipedia: "Speech synthesis".

* cited by examiner

METHOD AND MEDICAL IMAGING DEVICE FOR COMMUNICATION BETWEEN A CONTROL UNIT AND A PATIENT AND/OR AN OPERATOR

BACKGROUND OF THE INVENTION

1. Field of the Invention

The present invention concerns a method for a communication between a control unit of a medical imaging device (wherein the control unit is arranged within a control room) and an operator located in an examination room for a medical imaging examination and/or a patient located in the examination room and positioned on a patient support device, wherein the control room is arranged outside of the examination room.

2. Description of the Prior Art

For various medical questions, medical imaging examinations are implemented with a medical imaging device, for example a magnetic resonance device, a computed tomography device, a PET (positron emission tomography) device etc. In such medical imaging examinations, shorter examination times are always desirable, for cost reasons, as well as to be able to produce images of moving organs. For example, during the patient preparation increased attention by an operator in charge of the medical imaging examination in order to position the patient in a position on the patient support device that is correct for the medical imaging examination and/or for positioning accessory units (local coils, for example, in the case of magnetic resonance examinations) and/or an EKG unit. An incorrect positioning can lead to unwanted projections of incorrectly positioned objects beyond the patient support device, and therefore to damage of such incorrectly positioned objects upon movement of the patient bearing device (for example to squashing of cables and/or injuries to the patient etc.). The patient should also move as little as possible during the duration of the magnetic resonance examination, since movement can adulterate a measurement.

SUMMARY OF THE INVENTION

An object of the present invention is to provide a method and a device that permit a time-saving communication to take place between the control unit and an operator and/or patient located within the examination room during a preparation for a medical imaging examination and/or during the medical imaging examination.

The invention proceeds from a method to communicate between a control unit of a medical imaging device (wherein the control unit is arranged within a control room) and an operator located in an examination room for a medical imaging examination and/or a patient located in the examination room and positioned on a patient support device, wherein the control room is arranged outside of the examination room. The method includes acquisition of object data of objects positioned on the patient support device and/or of the operator by an object data acquisition unit, transfer of the acquired object data from the object data acquisition unit to the control unit, determination of information of the operator and/or of the objects positioned on the patient support device using the acquired object data, by means of the control unit, generation of output information using the determined information, and making the output information humanly perceptible within the examination room.

A particularly time-saving communication can be achieved (particularly during preparation of the patient) between the control unit arranged within the control room and the patient and/or operator located within the examination room, such that the operator no longer needs to leave the examination room for communication with the control unit. The control unit and a system control unit of the medical imaging device that are arranged within the control room have a direct output unit (for example a monitor) within the control room. A communication with the patient can also take place during the medical imaging examination. Furthermore, a particularly time-saving and quick monitoring of the objects arranged on the patient support device can take place, and therefore safety can be increased during the medical imaging examination (for example a magnetic resonance examination, a computed tomography examination and/or an additional medical imaging examination that appears reasonable to those skilled in the art). The workflow of the method according to the invention for the acquisition of object data of at least one object arranged on the patient support device of a medical imaging device enables a preparation and/or positioning of the patient on the patient support device to be monitored before the medical imaging examination, and enables the early detection of possible errors during the preparation and/or positioning of the patient on the patient table, and therefore the avoidance of errors in the medical imaging examination. By means of the output information, clinical personnel in charge of the medical imaging examination (in particular the operator) can additionally be quickly informed of a possible source of error during a preparation and/or positioning of the patient on the patient support device, such that an immediate error correction by the operator (and therefore a particularly time-saving preparation and/or positioning of the patient) can be achieved. Furthermore, the stressful situation for the patient that is caused by the medical imaging examination with the associated preparation of the patient can be shortened.

In this context, it should be understood that an "object arranged on a patient support device" can be a human patient or an accessory unit for the medical imaging examination, for example local coils for magnetic resonance examinations and/or an EKG unit, etc. The output information is different from the determined information of the object positioned on the patient support device.

The determined information of the object arranged on the patient bearing device can include position information and/or movement information during the medical imaging examination, so monitoring of the patient with regard to his or her position and/or with regard to unwanted movements can always take place during the medical imaging examination. A reaction to an unwanted motion of the patient during the medical imaging examination can be implemented particularly quickly. Restless patients can also be instructed (by means of the communication unit) to not move during the medical imaging examination, without the operator needing to visit the examination room.

The output information can include at least one item of safety information and/or an instruction for the patient and/or operator so that corresponding safety information is generated and presented as an output immediately by the control unit upon detection of a dangerous situation for the patient and/or the operator. The safety information and/or the instruction can also be presented as an output to the patient during the examination measurement, for example a breathing instruction, etc.

The safety instruction is preferably concerned with an erroneous positioning of the patient and/or additional objects on the patient support device, and/or concerned with possible risk regions during the preparation of the patient for the medical imaging examination. The information determined by the control unit can be compared with a safety value to determine the dangerous situation, which safety value can include a position query and/or a movement query. Only upon exceeding the safety value is output information with the warning notice generated by the control unit. The warning notice is presented as an output acoustically and/or optically within the examination space.

The output information may include at least one calming image and/or optical stimuli for the patient during the medical imaging examination, so the patient can be transitioned into a state that is advantageous to the medical imaging examination, namely a resting and/or calmed state, depending on the patient's mood and/or movements. The voice and/or motions of the patient are detected by the object data acquisition unit.

The acquisition of the object data can be an acquisition of optical 3D image data by means of a 3D image data acquisition unit. The 3D image data acquisition unit is preferably formed by conventional 3D scanners that have a large scan region (in particular the entire patient support device) with a precision of at most 10 mm, preferably of at most 5 mm, and particularly preferably of at most 3 mm, such that a cost-effective 3D image data acquisition unit is provided for the method. The 3D image data can include at least two image exposures that were acquired at different acquisition times, with the information of the object positioned on the patient bearing device being determined from these (at least two) image exposures. The acquisition of the 3D image data can take place together with an acquisition of physical features of the object on the patient support device and/or of the operator. Alternatively or additionally, the acquisition of the object data can take place as an acquisition of acoustic object data by means of an acoustic object data acquisition unit.

In a further embodiment of the invention, the output information is formed at least in part by acoustic speech output information, allowing the operator to continue to direct his or her optical attention on a patient preparation, for example, and can additionally be personally supplied with the output information.

Furthermore, the output information can include optical output information that is projected on a presentation surface within the examination room. The operator and/or the patient thus can be made aware of the output information particularly quickly and simply, and/or the output information can be detected by the operator and/or the patient. The optical output information can additionally include a calming image for the patient, on which image the patient concentrates during a medical imaging examination, and the patient therefore executes as few movements as possible that could interfere with the medical imaging examination. In this context, a presentation surface means a surface of a housing of the detector unit and/or a surface of the patient support device and/or a surface of the patient, with the optical output information being projected, and this surface being arranged, within a field of view of the operator and/or the patient.

The optical output information can be presented with a maximum contrast relative to the presentation area, such that an advantageous optical visibility of the optical output information can be achieved for the operator and/or the patient. The presentation surface and an environment of the presentation surface are detected by means of the object data acquisition unit (in particular the 3D image data acquisition unit) and evaluated by the control unit with regard to contrast and/or color composition, and the optical output information is subsequently generated by the control unit with a maximum contrast relative to the presentation surface.

The presentation surface can be selected depending on a viewing direction of the operator and/or the patient. A viewing direction of the operator and/or of the patient can be determined by means of the control unit from the acquired object data (in particular the optical object data), and a matching presentation surface for the optical output information within the environment of the operator and/or patient is subsequently determined by the control unit using the acquired object data. The patient and/or the operator thus can be comfortably informed of the optical output without the operator and/or patient needing to change his or her previous viewing direction. The operator can additionally receive the output information without interrupting his or her movement progression and/or workflow. Furthermore, a particularly fast information communication to the operator and/or the patient can take place.

In an alternative embodiment of the invention, the optical output information is included in a database of stored medical image information that is projected onto the patient, such that atlas images (for example) can be projected onto the scan region of the patient who is to be examined during a preparation of the patient for the medical imaging examination, and an advantageous monitoring is thereby provided to the operator for the selection of the scan region.

The optical output information also can include an optical control panel. The optical control panel is formed by a control panel image projected onto a presentation surface, so the patient, but more importantly the operator, can make an input at the optical control panel by gestures and/or acoustic commands. The detection of such gestures and/or acoustic commands can be made by the object data acquisition unit. A workflow thus can be optimized during a preparation of the patient for an impending medical imaging examination, since the operator can continue his or her activity at the patient but can nevertheless enter control commands via the optical control panel and/or make setting inputs via the optical control panel.

An advantageous adaptation of the optical control panel to a current situation and/or a current position (in particular of the patient) can be achieved in an embodiment wherein the position and/or size of the optical control panel is selected and/or varied by means of object data of the operator that is acquired by the object data acquisition unit. For example, a detected gesture by the operator can be interpreted by the control unit as operating a slider of the optical control panel by the operator, and a scan region of the patient and/or a homogeneity region of a detector unit at the patient thus can be established by said operator. Alternatively, the optical control panel can be selected and/or variably configured by the operator by means of a speech input by the operator that is detected as acoustic object data.

Furthermore, a response of the operator and/or of the patient can be detected by means of acoustic and/or optical object data after the presentation of the output information, so a communication between the control unit and the operator and/or the patient can be achieved. For example, at least a partial control of the medical imaging device can be achieved without the operator needing to leave the examination room. Moreover, the operator can react particularly quickly to changes in the examination room and/or the patient (for example a patient position).

The acoustic and/or optical object data that are detected as the response of the operator and/or the patient can be interpreted by the control unit as an input of settings and/or a control command. A change and/or input of control parameters and/or control settings for the medical imaging examination and/or settings that are required for a preparation of the patient can therefore take place by means of the detected acoustic and/or optical object data of the operator. The change and/or input of the settings and/or of the control commands by the operator thus can take place within the examination room without the operator needing to leave the examination room for this purpose. An optimized (and in particular time-saving) workflow thus can be enabled during a preparation of the patient for the medical imaging examination.

In a further embodiment of the invention, additional output information is generated depending on information determined from the response. For example, the operator can be notified of the changes he or she has made (for example whether they are within permissible setting ranges, etc.). The operator can additionally receive a control and/or a confirmation of the input that the operator has made by means of the acquired object data. The additional output information can include acoustic output information and/or optical output information.

The presentation of the output information can include the execution of the control command, so a time-saving and comfortable (at least partial) control of the medical imaging device and/or of the medical imaging examination can be achieved for the operator. The operator thus can be within the examination room for at least a portion of the control of the medical imaging device and/or the medical imaging examination, and does not need to stay in the control room to enter control commands and/or to enter parameters and/or adjustments.

The additional output information can include an additional optical control panel that is projected onto the presentation surface within the examination room, via which corrections of settings and/or an adaptation of inherently modified conditions can be made particularly quickly by the operator. The additional optical control panel can be projected onto the presentation surface in addition to a first optical control panel or instead of the first optical control panel. It is also possible for the additional optical control panel to be projected onto a further projection surface that is different from the presentation surface of the first optical output information and/or of the first optical control panel.

In a further embodiment of the invention, the acquisition of acoustic object data and of optical object data takes place simultaneously, such that position changes and/or gestures of the patient and/or operator and the output of acoustic commands and/or acoustic information can be detected simultaneously. This allows different workflows to take place simultaneously within the control unit in a time-saving manner. For example, a correct position of the patient and/or additional objects on the patient support device can be monitored by the control unit by means of the optical acquisition of object data. At the same time, speech commands of the operator (for example for a positioning of the bed table) can also be detected by the acoustic acquisition unit. An evaluation of the acoustic object data and the optical object data also takes place simultaneously within the control unit. For example, a correct position of the patient and/or additional objects on the patient support device can be monitored by the control unit by means of the optical acquisition of object data. At the same time, speech commands of the operator (for example for a positioning of the bed table) can also be detected by the acoustic detection unit. An evaluation of the acoustic object data and the optical object data also take place simultaneously within the control unit.

The output information can be emitted both acoustically and optically, so that a high safety standard can be achieved for operation of the medical imaging device. For example, the operator can be notified both by the optical output information and by the acoustic output information of a possible incorrect positioning of the patient and/or additional objects positioned on the patient support device. The acoustic output information and the optical output information can be emitted simultaneously.

The invention also encompasses a medical imaging device with a detector unit that has a patient receptacle region and a patient support device and that is arranged within a shielded examination room, a control unit arranged in a control room outside of the shielded examination room, and a communication unit that includes a 3D image data acquisition unit that is designed to acquire patient information and/or optical object data of an operator, and a projection unit for communication between the control unit and an operator and/or patient located in the examination room.

An optical control panel can be projected by the projection unit onto a presentation surface in the examination space. A workflow during a preparation of the patient thus can be optimized for a pending medical imaging examination, since the operator can continue his or her activity at the patient and can nevertheless establish control commands by means of the optical control panel and/or make adjustments and/or be informed of current dangerous situations. In addition, the operator and/or the patient can particularly quickly and simply be informed by a visual detection at the control panel.

Furthermore, the optical control panel can be projected onto an external housing of the detector unit and/or onto the patient support device and/or onto the patient by the projection unit, and the optical control panel can be projected depending on a viewing direction of the operator within the examination room. For this purpose, the viewing direction of the operator is detected by the 3D image data acquisition unit, and the 3D image data are additionally evaluated by the control unit in order to select an appropriate presentation surface.

In an embodiment, at least one control command made at the optical control panel in the form of a gesture of the operator and/or of the patient within the examination room can be detected by the 3D image data acquisition unit, so a workflow during a preparation of the patient can be optimized for a pending medical imaging examination since the operator can continue his or her activity at the patient but can nevertheless enter control commands via the optical control panel. Furthermore, communication between the control unit and the operator and/or the patient can be achieved, so that operator-driven control of the medical imaging device can be achieved without the operator having to leave the examination room. Moreover, the operator can react particularly quickly to changes in the examination room and/or of the patent, and the control command can be adapted particularly quickly to changing conditions within the examination room. Alternatively or additionally, the input and/or selection of settings and/or of control commands and/or of additional parameters can take place by the detection of acoustic commands by an acoustic object data acquisition unit.

A particularly flexible adjustment and/or alignment of the focus (in particular with regard to a viewing direction of the operator and/or of the patient) of the projection unit can be achieved in an embodiment wherein the communication unit has at least one positioning unit for spatial alignment and/or a spatial adjustment of the projection unit within the examination room. In this context, a spatial alignment and/or a spatial adjustment of the projection unit means a spatial alignment and/or a spatial adjustment of an optical axis of the projection unit. The positioning unit can be a motor unit (for example an electric motor) and/or force transfer unit and/or an energy transfer unit (in particular a mechanical force transfer unit and/or energy transfer unit) between the motor unit and the projection unit.

Furthermore, a particularly flexible adjustment and/or alignment of the focus of an acquisition region of the 3D image data acquisition unit can be achieved in an embodiment wherein the communication unit has at least one positioning unit for spatial adjustment and/or a spatial alignment of the 3D image data acquisition unit within the examination room. In this context, spatial alignment and/or a spatial adjustment of the 3D image data acquisition unit mean spatial alignment and/or spatial adjustment of an optical axis of the 3D image data acquisition unit. The positioning unit can be a motor unit (for example an electric motor) and/or a force transfer unit and/or an energy transfer unit (in particular a mechanical force transfer unit and/or energy transfer unit) between the motor unit and the 3D image data acquisition unit.

Preferably, the positioning unit for spatial alignment and/or spatial adjustment of the projection unit and/or the positioning unit for spatial alignment and/or adjustment of the 3D image data acquisition unit are arranged within the control room. Interference with the medical imaging device during a medical imaging examination thus can be prevented, for example interference with a magnetic resonance examination that is caused by an electric motor.

In a further embodiment of the invention, the 3D image data acquisition unit has an optical axis and that the projection unit has an optical axis, and the alignment of the optical axis of the 3D image data acquisition unit is variable relative to an alignment of the optical axis of the projection unit. The adjustment and/or alignment of the projection unit can take place independently of the adjustment and/or alignment of the 3D image data acquisition unit. The projection unit thus can be aligned particularly flexibly with regard to the position of the operator and/or the patient.

In a space-saving embodiment of the projection unit and/or the 3D image data acquisition unit, the projection unit and/or the 3D image data acquisition unit is arranged on a wall of the examination room.

In an embodiment wherein the communication unit has an acoustic detection unit for detection of acoustic object data of the operator and/or of the patient, a redundant acquisition unit can detect gestures of the operator and/or of the patient and acoustic speech signals of the operator and/or of the patient. The acquisition of optical object data (in particular detection of 3D image data) and the detection of acoustic object data (in particular detection of acoustic speech signals) can take place simultaneously.

In a further embodiment of the invention, the control unit evaluates the object data acquired by the communication unit and generates at least one acoustic signal (for example a speech signal, an acoustic information) depending on this information, so the patient and/or the operator can be notified of the output information depending on a viewing direction. For this purpose, the communication unit also has an acoustic output unit to emit the acoustic signal (in particular a speech signal) into the examination room.

A particularly compact control unit can be achieved in an embodiment wherein control of the communication unit takes place by means of the control unit. The control unit then is a single control unit that controls both the 3D image data acquisition unit, the projection unit, the acoustic object data acquisition unit and the acoustic output unit. The control unit is preferably synchronized with a system control unit of the medical imaging device. The control unit can also be integrated within the system control unit.

DESCRIPTION OF THE PREFERRED EMBODIMENTS

Figure 1:
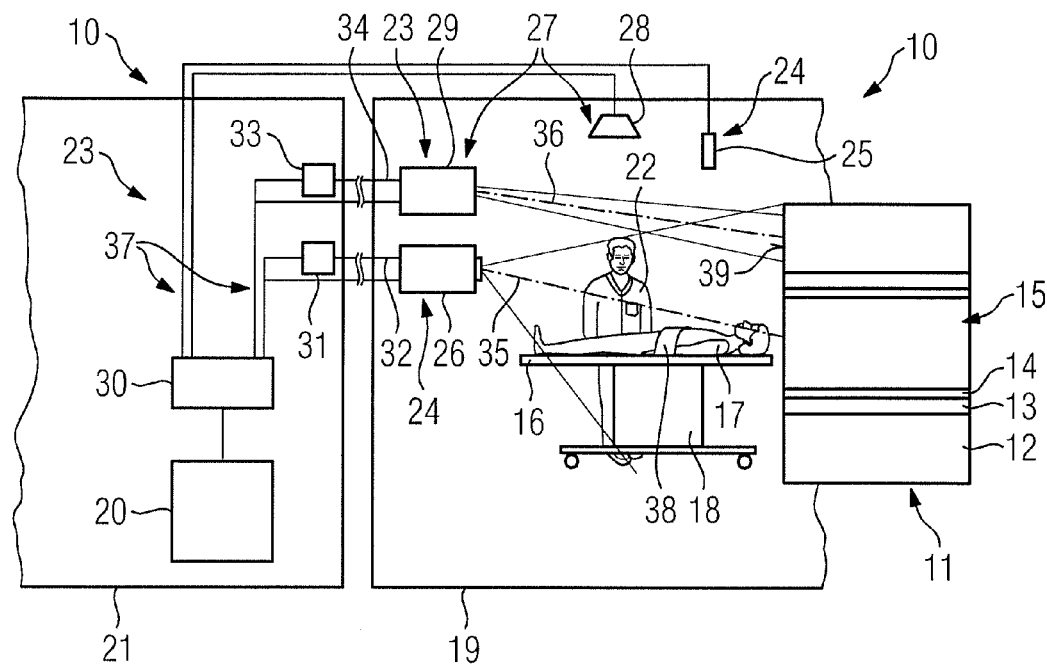
FIG. 1 shows an embodiment of the medical imaging device according to the invention, with a communication unit, in a schematic presentation.

A medical imaging device 10 formed by a magnetic resonance device is schematically presented in FIG. 1. As an alternative, the medical imaging device 10 can be formed by a computed tomography device and/or a PET device and/or additional medical imaging devices 10 that appear to those skilled in the art to be reasonable.

The magnetic resonance device has a detector unit 11 that—in the present exemplary embodiment—includes a magnet unit with a basic magnet 21, a gradient coil unit 13 and a radio-frequency coil unit 14. Furthermore, the magnetic resonance device has a cylindrical patient receptacle region 15 to accommodate a patient 17 positioned on a bed table 16. The cylindrical patient receptacle region 15 is cylindrically surrounded by the detector unit 11.

To support the patient 17, the magnetic resonance device has a patient bearing device 18 with a bed table 16. The patient 17 is positioned on this bed table 16 and, together with the bed table 16, is driven into the patient receptacle region 15 for a medical imaging examination. The detector unit 11 and the patient support device 18 are arranged within an examination room 19, wherein the examination room 19 shields the detector unit 11 from interference fields (in particular magnetic and/or electric interference fields).

The magnetic resonance device has a system control unit 20 to control the medical imaging examination, in particular a magnetic resonance examination, wherein the system control unit 20 is arranged in a control room 21. The control room 21 is arranged to be separate from and in particular outside of the examination room 19. The system control unit 20 has a processor and a memory unit in which are stored different control programs for an operation of the magnetic resonance device. The individual control programs are executed by the processor.

A preparation of the patient 17 on the patient bearing device 18 is attended to by an operator 22 (in particular an operator 22 in charge of the magnetic resonance measurement) within the examination room 19. The control of the magnetic resonance examination and/or individual partial regions of the magnetic resonance device takes place exclusively via the system control unit 20.

The magnetic resonance device has a communication unit 23 for an efficient communication between the system control unit 20 within the control room 21 and the operator 22 and/or the patient 17 within the examination room 19. The communication unit 23 has an object data acquisition unit 24 that has an acoustic object data acquisition unit 25 that (in the present exemplary embodiment) is formed by a microphone and an optical object data acquisition unit 26 formed by a 3D image data acquisition unit. The communication unit 23 also has an output unit 27 that includes an acoustic speech output unit 28 (that is formed by a speaker in the present exemplary embodiment) and an optical output unit 29 formed by a projector. The communication unit 23 can have more than one 3D image data acquisition unit and/or more than one optical output unit 29. Furthermore, it is possible for the communication unit 23 to have more than one acoustic object data acquisition unit 25 and/or more than one speech output unit 28.

Furthermore, the communication unit 23 has a control unit 30. In the present exemplary embodiment, the communication unit 23 has a single control unit 30 to control the acoustic object data acquisition unit 25, the 3D image data acquisition unit, the acoustic speech output unit 28 and the optical output unit 29. However, in principle it is also conceivable that the communication unit 23 has multiple control units 30 for a separate control of the acoustic object data acquisition unit 25 and the acoustic speech output unit 28 by the 3D image data acquisition unit and the optical output unit 29.

In the present exemplary embodiment, the control unit 30 of the communication unit 23 is designed separate from the system control unit 20. However, in an alternative embodiment of the invention the control unit 30 of the communication unit 23 can be integrated within the system control unit 20. The control unit 30 is synchronized with the system control unit 20.

The object data acquisition unit 24 and the output unit 27 are arranged within the examination room 19. In contrast to this, the control unit 30 of the communication unit 23 is arranged within the control room 21.

The 3D image data acquisition unit and the projection unit are arranged on one wall of the examination space 19. The object data acquisition unit 24 has positioning units 31, 32 for spatial alignment and/or spatial adjustment of the 3D image data unit within the examination space 19. A positioning unit 31—formed by a motor unit, for example an electric motor unit—is arranged within the control room 21. Transmission of a mechanical force and/or energy to the 3D image data acquisition unit for the spatial positioning and/or spatial adjustment takes place via an additional positioning unit 32 that includes suitable transmission means. The communication unit 23 likewise has positioning units 33, 34 for spatial alignment and/or spatial adjustment of the projection unit. A positioning unit 33—formed by a motor unit, for example an electric motor unit—is arranged within the control room 34. Transmission of mechanical force and/or energy to the projection unit for the spatial positioning and/or spatial adjustment takes place via additional or positioning unit 34 that includes suitable transmission means. Control of the positioning units 33, 34 for spatial alignment and/or spatial adjustment of the projection unit is independent of the control of the positioning units 31, 32 for spatial alignment and/or spatial adjustment of the 3D image data acquisition unit. The control of the positioning units 33, 34 for spatial alignment and/or spatial adjustment of the projection unit and the control of the positioning units 31, 32 for spatial alignment and/or spatial adjustment of the 3D image data acquisition unit takes place by means of the control unit 30. It is therefore possible for the optical axis 35 of the 3D image data acquisition unit to be aligned differently from the optical axis 36 of the projection unit, or for the alignment of the optical axis 35 of the 3D image data acquisition unit to be variable relative to an alignment of the optical axis 36 of the projection unit.

The acoustic object data acquisition unit 25 and the acoustic speech output unit 28 are likewise arranged within the examination room 19. The communication unit 23 can have a positioning unit for an alignment of the acoustic object data acquisition unit 25 and/or the acoustic speech output unit 28.

The object data acquired by the acoustic object data acquisition unit 25 and the 3D image data acquisition unit are relayed via a data transmission unit 37 to the control unit 30. The output information is likewise relayed by the control unit 30 via the data transmission unit 37 to the acoustic speech output unit 28 and the projection unit. For this purpose, the data transmission unit 37 can have a data line or be designed for a wireless data transfer.

Figure 2:
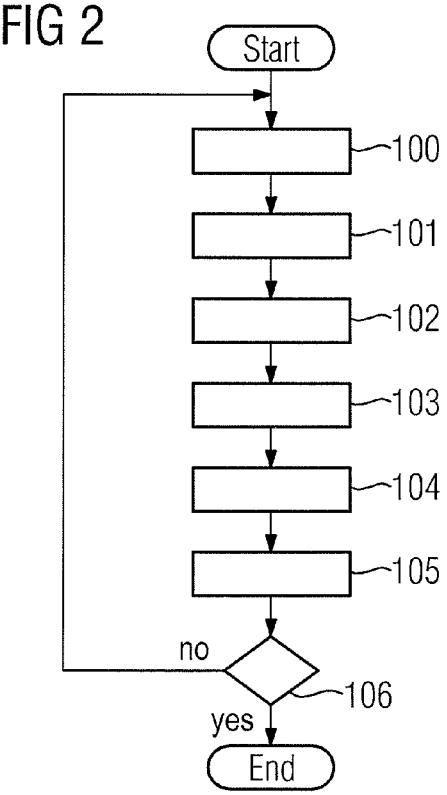
FIG. 2 illustrates an embodiment of the method according to the invention.
Figure 3:
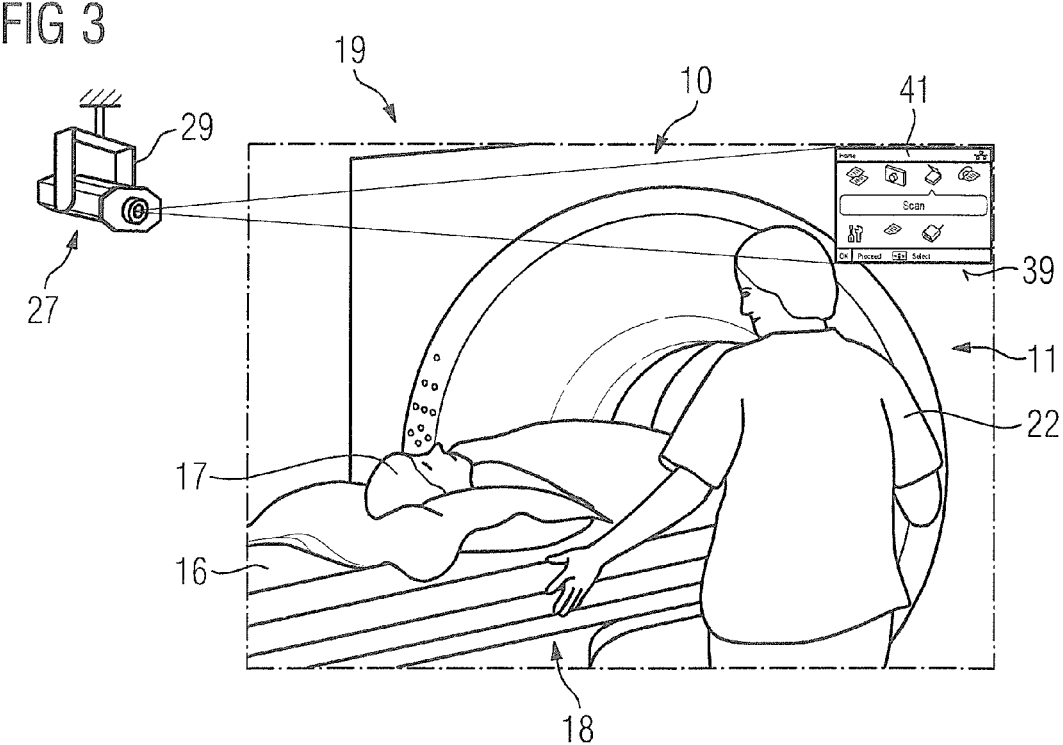
FIG. 3 shows a first exemplary embodiment of a projection of an optical control panel on a housing of a detector unit.

A method according to the invention for a communication between the control unit 30 and the operator 22 and/or the patient 17 is schematically shown in FIG. 2.

The method according to the invention preferably starts at the beginning of a preparation of the patient 17 for the pending medical imaging examination. During the preparation, the patient 17 is positioned on the patient bearing device 19 and further objects (in particular accessory units 38 such as local coils and/or an EKG unit etc.) are likewise additionally positioned on the patient bearing device 19 and/or on the patient 17.

Initially, in a first method step 100 object data of the objects positioned on the patient bearing device 19 (in particular the patient 17 and/or the accessory units 38) and of the operator 22 are detected by means of the object data acquisition unit 24, and a situation during the preparation of the patient 17 within the examination room 19 is therefore detected. The acquisition of optical object data (that are formed by 3D image data in the present exemplary embodiment) hereby takes place by means of the 3D image data acquisition unit, and the acquisition of acoustic object data takes place by means of the acoustic object data acquisition unit 25. A focus of the 3D image data acquisition unit and a direction of the acoustic object data acquisition unit 25 are hereby directed towards a region of the operator 22 and/or of the patient 17 together with the patient bearing device 18.

The acquisition of the acoustic object data and the acquisition of the optical object data (in particular the 3D image data) can take place simultaneously, such that a maximum of information is present at the control unit 30.

The acquired object data are subsequently transferred to the control unit 30 by means of the data transfer unit 37 in a further method step 101 and are evaluated there, wherein the control unit 30 has the necessary evaluation programs and/or control programs for this that run on a processor of said control unit 30.

In the subsequent method step 102, the control unit 30 determines an information of the object positioned on the patient bearing device 18 and/or of the operator 22 exclusively using the acquired object data. This information can include a movement information of the patient 17 and/or of the operator 22, for example, and/or a spatial extent of the patient 17 and/or of accessory units 38. Different program units that determine the different information using the 3D image data run within the control unit 30 for this.

In this method step 102, different image exposures that image an identical spatial region but were acquired at different measurement times—in particular a movement information of the patient 17 and/or of the operator 22—are thus determined from the 3D image data. The differences—in particular with regard to a position and/or attitude and/or orientation of the patient 17 and/or of the operator 22—are determined between the individual image exposures by means of a difference calculation, and a movement and/or a gesture of the patient 17 and/or of the operator 22 is derived from this.

Furthermore, in this method step 102 physical features of the objects positioned on the patient bearing device 18 and/or of the operator 22 are detected and/or determined using image exposures of the 3D image data, and the information of the object positioned on the patient bearing device 18 and/or of the operator 22 is determined by means of the detected physical features. For example, the physical features can include a skeletal outline of the patient 17 and/or of the operator 22; and/or extremities and/or articulation points or articulation axes; and/or a view of the patient 17 and/or of the operator 22. In addition, individual body regions of the patient 17 (for example articulation regions) can be provided with marker elements. A support position and/or an orientation of the patient 17 on the patient bearing device 18 thus can be detected, for example a ventral position or a dorsal position of the patient 17 and/or a position in which the patient 17 is slid feet-first into the patient receptacle region 15 by means of the patient bearing device, or a position in which the patient 17 is moved head-first into the patient receptacle region 15 by means of the patient bearing device. In addition, a detection of a position information of the patient 17 (in particular of individual body parts, for example extremities) and their positioning relative to one another is also possible, such that a closed or annular arrangement of the extremities of the patient 17 can be detected.

In addition to the position information, dimension information and/or size information of the object and/or of the patient 17 can be determined using the 3D image data within the control unit 30, such that a projection of body parts of the patient 17 and/or a projection of accessory units 38 beyond the patient bearing device 17 can be detected. For example, a mass distribution of the patient 17 can be calculated by the detection of dimension information. Moreover, position information and/or support information and/or an orientation of the accessory units 38 can be acquired.

Furthermore, in the method step 102 a detection and/or registration of the patient 17 is also possible by execution of a program for face recognition within the control unit 30. A patient 17 detected in such a manner can be compared by means of the control unit 30 with patient information stored in the measurement parameters.

In addition to the evaluation of the optical object data, an evaluation of the acoustically detected object data also takes place by means of the control unit 30 in this method step 102. The evaluation of the acoustically detected object data can take place separately from the optical object data, or (preferably) can be combined with the evaluation of the optical object data. For example, a speech command and/or a spoken statement within the acoustic object data can be determined by the control unit 30 and—together with an information of the optical object data of this speech command and/or this spoken statement—be associated with the operator 22 and/or the patient 17.

An additional method step 103 to generate an output information follows the method step 102 of the determination of the information of the objects positioned on the patient bearing device 18 and/or of the operator 22. The output information is generated by the control unit 30 using the information of the operator 22 and/or the objects positioned on the patient bearing device 18. Information and/or data that are stored in a storage medium of the control unit 30 and/or the system control unit 20 and/or a database (for example patient-related data) can also be considered by the control unit 30 to generate the output information.

The output information can include a safety instruction to the patient 17 and/or to the operator 22. The safety instruction can indicate, for example, a position of the patient 17 that is incorrect for the pending medical imaging examination (in particular a position with closed loops or an annular arrangement of the extremities of the patient 17) and/or support of the patient 17 that is incorrect for the pending medical imaging examination etc. In addition to this, it is also conceivable that the safety instruction indicates to the operator 22 an incorrect positioning of the accessory units 38 and/or cables and/or accessory elements overhanging the bed table 16 that can lead to damage to a cable and/or the accessory elements given a movement of the bed table 16. In addition, a safety instruction can be generated by the control unit 30 in the method step 103 even given the lack of a presence of an acute danger, wherein the safety instruction has a function of a notification of a possible danger source, such that the operator 22 is again informed of the possible danger sources before a start of the medical imaging examination.

Furthermore, the output information can include an instruction for the patient 17 and/or the operator 22. For example, the instruction include a next step within the workflow executed by the operator 22 during the preparation of the patient 17 on the patient bearing device 18, and/or an instruction to the patient 17 with regard to a behavior during the medical imaging examination.

The output information can additionally include a request to the operator 22 by means of which said operator 22 is requested to enter information and/or parameters and/or commands.

The output information can include an acoustic output information and/or an optical output information, wherein the output information is output within the examination room 19 by means of the acoustic speech output unit 28 and/or the optical output unit 29 of the output unit 27 in a further method step 104. Insofar as the output information includes an optical output information, this optical output information is presented on a presentation surface 39 within the examination room 19 in a further method step 104. For this, an environment surrounding the operator 22 and/or the patient 17 is evaluated by the control unit 30 with regard to a possible presentation surface 39 using the acquired optical object data (in particular the 3D image data). The selection criteria of the control unit 30 for the presentation surface 39 can be dependent on the optical output information. For example, if the output information includes one or more safety instructions with regard to the positioning of the patient 17 on the patient bearing device 18, it is reasonable for the presentation surface 39 to be arranged in the possible danger region and/or near said possible danger region.

In addition to this, a viewing direction of the observer (in particular of the patient 17 and/or of the operator 22) can be taken into account by the control unit 30 in the selection of the presentation surface 39, and the presentation surface 39 can be selected depending on a field of view of the patient 17 and/or of the operator 22. The presentation surface 39 can in principle be formed by any surface present within the examination room. However, the presentation surface 39 is particularly advantageously formed by a surface of an external housing of the detector unit 11 that faces towards the operator 22 and/or the patient 17 and/or by a surface of the patient 17 and/or of the patient bearing device 18 that faces toward the operator 22. The medical imaging device 10 can have additional presentation surfaces 39 that are additionally arranged at the detector unit 11 for presentation and/or output of the optical output information.

The optical output information is projected onto the presentation surface 39 or, respectively, onto multiple individual presentation surfaces 39 by means of the projection unit. For the optical output information, before an output and/or presentation of said optical output information, a brightness and/or a presentation color that has a maximum contrast relative to the respective presentation surface 39 is determined by the control unit 30 for said respective optical output information.

Figure 9:
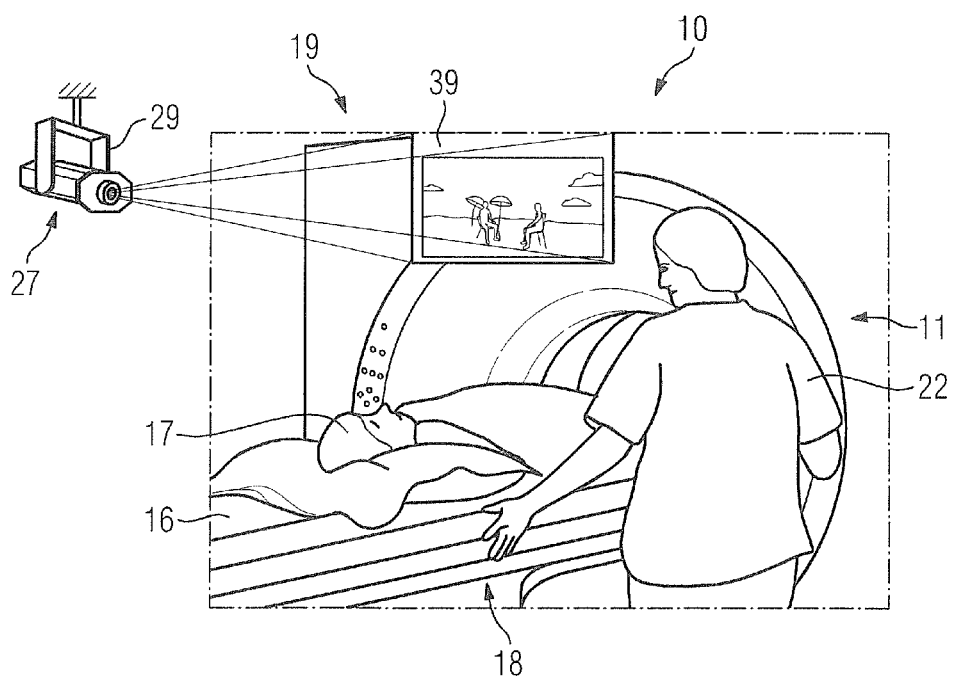
FIG. 9 shows an exemplary embodiment of a projection of a viewing surface for the patient.

For example, if the optical output information is a calming image on which the patient 17 can concentrate during the medical imaging examination, this optical output information is projected onto a presentation surface 39 that is visible to the patient (as this is depicted in FIG. 9). Optical stimuli can also additionally be presented on the presentation surface 39 for the patient 17. The optical output information in the form of calming images and/or optical stimuli for the patient 17 are preferably emitted and/or presented during the medical imaging examination. An optical and/or acoustic output of instructions to the patient 17 during the medical imaging examination is also conceivable, in particular an output of breathing instructions etc.

In the present exemplary embodiment, the presentation surface 39 is formed by a surface designed for the presentation (FIG. 9). However, in principle it is also conceivable that the presentation surface 39 is formed by a surface of a housing wall of the detector unit 11. In addition to this, it is also conceivable that the presentation surface 39 is arranged within the patient receptacle region 15, and the optical output information is projected into the patient receptacle region 15 by means of the projection unit and additional auxiliary means (in particular projection mirrors etc.). The method according to the invention is also executed during the medical imaging examination for the creation of output information during said medical imaging examination. For this purpose, the object data acquisition unit 24 (in particular a focus of the object data acquisition unit 24) is concentrated on a region within the patient receptacle region 15, such that object data of the patient 17 are acquired even during the medical imaging examination. Using the acquired object data, a movement information of the patient 17 and/or support information of the patient 17 are determined within the control unit 30 in method step 102, and the output information is generated from these in method step 103.

Figure 7:
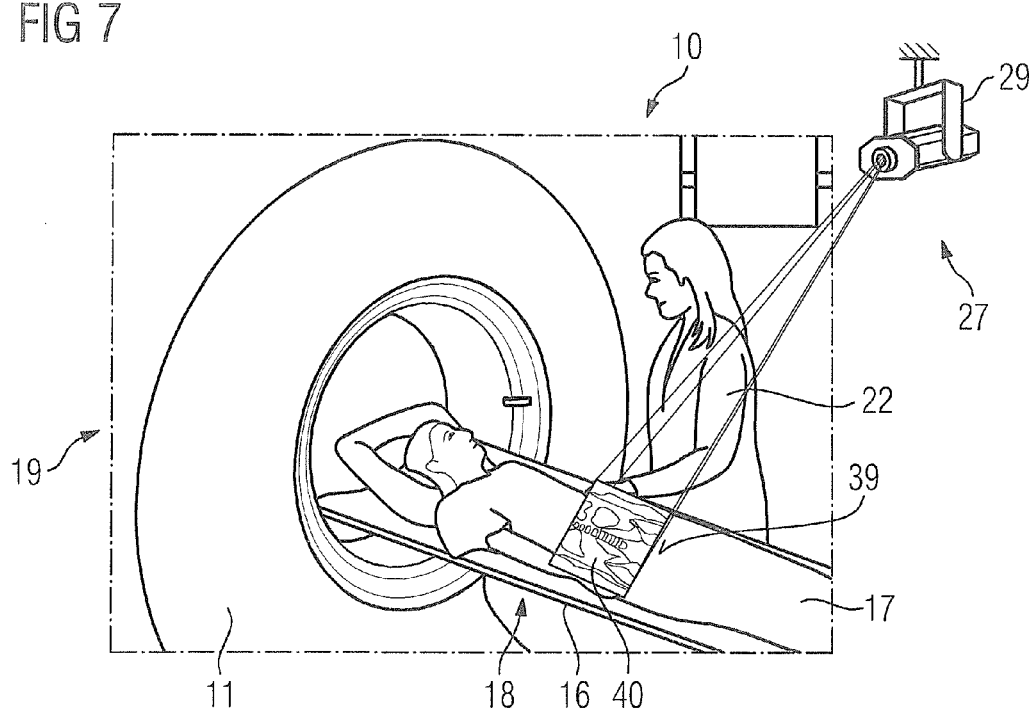
FIG. 7 shows a fourth exemplary embodiment of a projection of an optical control panel on the patient.

In addition to this, the optical output information can also be formed by a medical image information, for example an atlas image 40 of the patient 17. This medical image information is stored within a database. Furthermore, the optical output information can include additional patient-specific information. During the preparation of the patient 17 for the medical imaging examination, this optical output information is projected onto the region of the patient 17 that is relevant to the pending medical imaging examination. By means of the medical image information and/or the patient-related information, the operator 22 can implement monitoring as to whether a correct selection of a body region of the patient 17 has been prepared for the pending medical imaging examination during the preparation (FIG. 7), for example.

The optical output information can additionally include an optical control panel 41 that is projected onto the presentation surface 39 (FIGS. 3-6 and 8). By means of the optical control panel 41, the operator 22 and/or the patient 17 can make a selection of settings at the optical control panel 41 via gestures and/or acoustic commands, wherein the selection that is made is detected optically or acoustically by means of the acoustic object data acquisition unit and/or the 3D image data acquisition unit.

Furthermore, the output information can also include an acoustic output information (for example an acoustic speech output). In method step 104, the acoustic output information can be output simultaneously with the optical output information by the acoustic speech output unit 28, wherein a control of the simultaneous output of the acoustic output information and the optical output information takes place by means of the control unit 30. However, in addition to this it is also conceivable for the acoustic output information to be emitted separately (in terms of time) from the optical output information by means of the acoustic speech output unit 28.

Furthermore, during the generation of the output information and/or the output and/or presentation of the output information object data are acquired within the examination room by the object data acquisition unit 24 (in particular the optical 3D image data acquisition unit and the acoustic object data acquisition unit 25), and the object data are transferred to the control unit 30. A continuous evaluation of the acquired object data takes place there, such that situation changes and/or critical situations can be reacted to particularly quickly via the generation and the output and/or presentation of the output information.

After the output and/or presentation of the output information, a response to the output information by the operator 22 and/or the patient 17 takes place in a further method step 105. This response of the operator 22 and/or of the patient 17 is detected by means of the object data acquisition unit 24 in the method step 100. The response of the operator 22 and/or of the patient 17 can include a speech input (for example a speech command) and/or an optical response in the form of a gesture of the patient 17 and/or of the operator 22.

Figure 5:
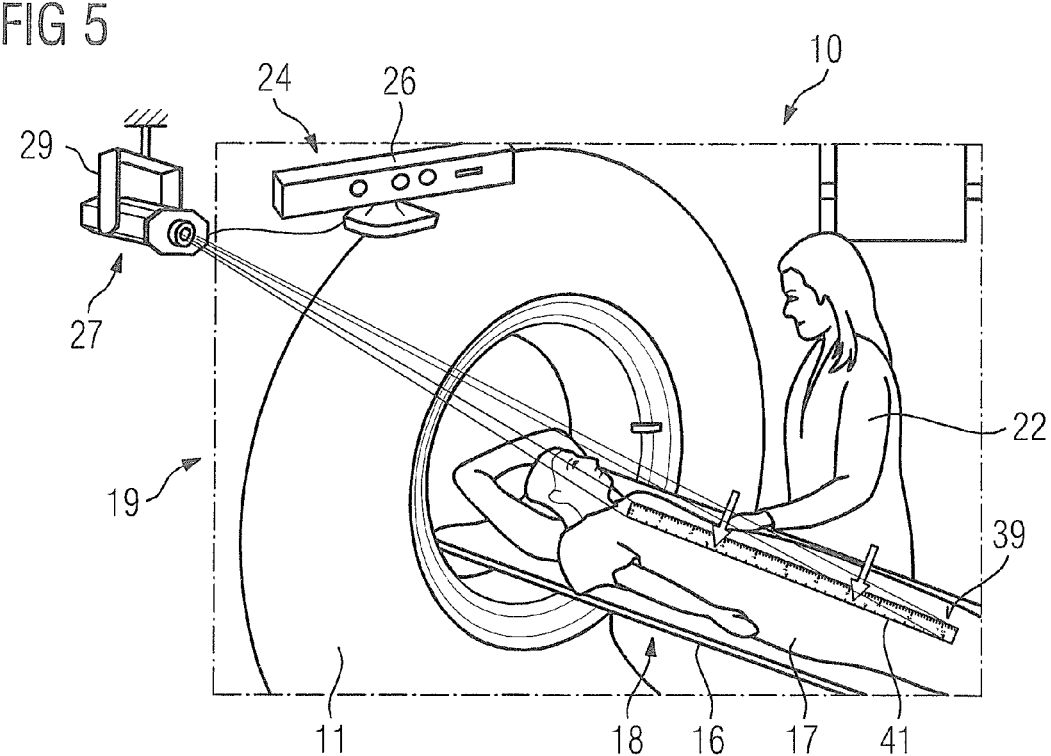
FIG. 5 shows a second exemplary embodiment of a projection of an optical control panel on the patient.
Figure 6:
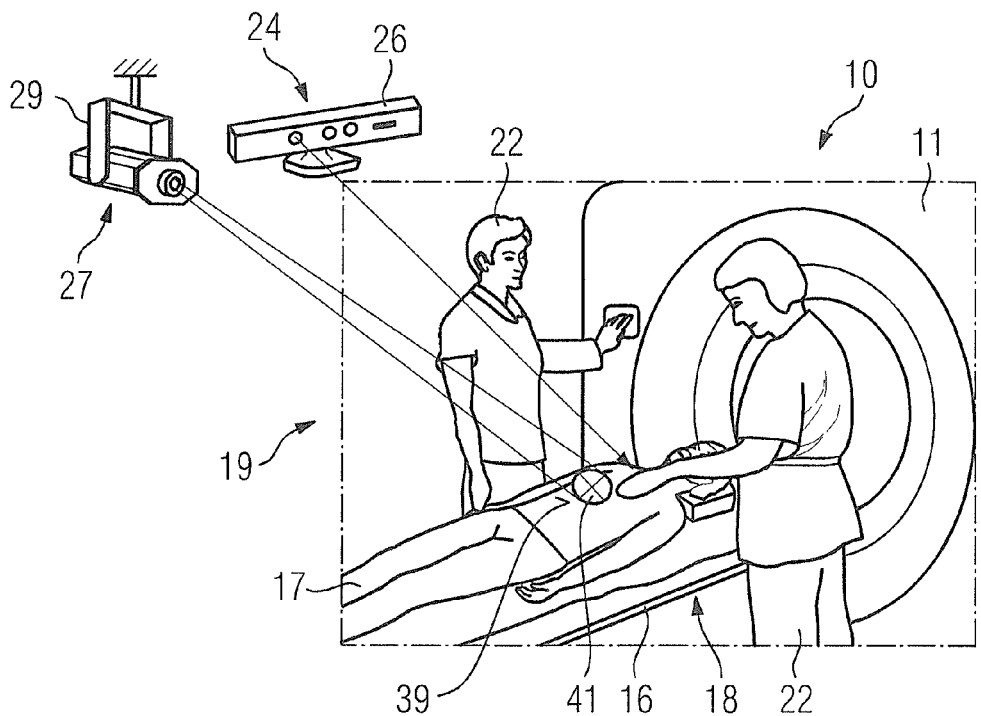
FIG. 6 shows a third exemplary embodiment of a projection of an optical control panel on the patient.

For example, the response of the operator 22 can be formulated to cause a position of the optical control panel 41 and/or an additional optical output information and/or a size of the optical control panel 41 and/or an additional optical output information to be selected and/or varied at the presentation surface 41 by means of the acquired object data, as is shown in FIGS. 5 and 6. For this purpose, the optical control panel 41 and/or the additional optical output information is initially presented at the presentation surface 39 in method step 104. A repositioning of the optical control panel 41 and/or of the additional optical output information can take place using a gesture of the operator 22 (for example a placement of a hand of the operator 22 on the optical control panel 41 and/or the additional optical output information and a subsequent shifting of the hand), in that this gesture is detected by the 3D image data acquisition unit in the following method step 100 and is interpreted by the control unit 30 as a repositioning gesture in the method step 103. Furthermore, for example, a placement of the hand of the operator 22 at an edge region of the optical control panel 41 and/or of the additional optical output information and a subsequent shifting of the hand can be interpreted as an adaptation of the size of the optical control panel 41 and/or of the additional optical output information. The detected object data must satisfy all criteria within the control unit 30 for a repositioning and/or an adaptation of the size of the optical control panel 41, and a control command for the repositioning and/or an adaptation of the size of the optical control panel 41 is respectively associated with unique and selected gestures and/or movements of the operator 22 in connection with the optical control panel 41. Using the control command determined by the control unit in the method step 103 using the detected object data, a control instruction is generated in method step 104 and this control instruction is executed in method step 105.

For example, in FIG. 5 the optical control panel 41 is formed by a scale that is presented as a presentation surface 39 on the patient 17. In the present exemplary embodiment, two arrows on the scale represent a scan region for the pending medical imaging examination. The scan region can be exactly established by the operator 22 by sliding these arrows along the scale, wherein the operator 22 hereby executes a gesture and/or a movement of a displacement of these arrows with his hands. This movement and/or gesture of the operator 22 is detected by the 3D image data acquisition unit in method step 100 and evaluated by the control unit 30 in method step 102. The acquired object data must hereby satisfy all criteria for a displacement within the control unit 30, wherein a control command for the displacement is associated with unique and selected gestures and/or movements of the operator 22 in connection with the optical control panel 41. Newly generated output information is subsequently presented at the presentation surface 39 by the projection unit in method step 104. This type of presentation and/or establishment of the scan region can additionally be combined with a presentation from FIG. 7, and an atlas image 40 of the patient 17 can additionally be projected onto the relevant region.

Furthermore, as is apparent from FIG. 6 a central detection region—for example a homogeneity region and/or a field of view of a magnetic resonance device for a magnetic resonance examination (the pending medical imaging examination)—can be marked via a projection of an optical output information on the patient 17 and be shifted to a desired position by means of a gesture of the operator 22. Displacement of the control panel 41 takes place analogous to the Specification with regard to FIG. 5.

In addition to this, settings and/or parameters for the pending medical imaging examination can also be changed by means of the response of the operator 22. For example, for this purpose the optical control panel 41 has a menu selection projected onto the presentation surface 39, for example as this is presented in detail in FIG. 3. Here a selection can be made at the optical control panel 41 by means of a gesture of the operator 22 that is detected by means of the optical 3D image data acquisition unit, for example in that the gesture includes tapping and/or resting a hand and/or a partial region of the hand of the operator 22 on the presentation surface 39 with the control panel 41, in particular the partial region of the optical control panel 41 that includes the desired selection option. For the operator, the input and/or selection at the optical control panel 41 takes place analogous to an input and/or selection at a touchscreen. A detection of the response of the operator 22 and a subsequent evaluation within the control unit 31 take place analogous to the Specification with regard to FIG. 5, wherein the acquired object data must satisfy all criteria within the control unit 30 for a selection of settings and/or parameters. A control command for the selection of settings and/or parameters is hereby respectively associated with unique and selected gestures and/or movements of the operator 22 in connection with the optical control panel 41. The optical output information changes in method steps 103 and 104 due to the selection that is made, such that a modified output information can be output to acknowledge the operator 22. The optical and/or acoustic output information can additionally include a safety query in which the operator 22 and/or the patient 17 must again confirm the input he has made. This input can take place both acoustically and/or optically.

Figure 4:
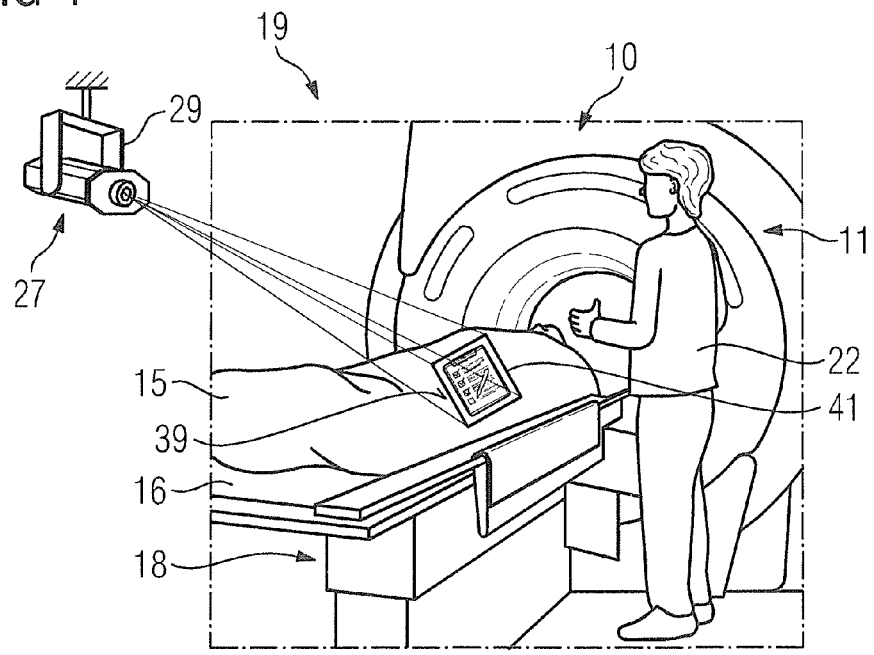
FIG. 4 shows a first exemplary embodiment of a projection of an optical control panel on the patient.

In FIG. 4, the optical control panel 41 is formed by a control list of individual preparation steps for the preparation of the patient 17 for the pending medical imaging examination. These preparation steps must be executed by the operator 22 before the medical imaging examination. This control list is projected to the operator 22 within his field of view of the patient 17, wherein the operator 22 can and/or must confirm the individual preparation steps in this control list. This takes place via a gesture of a virtual checking off of the individual preparation steps on the control list, wherein the gesture of the operator 22 is detected in method step 100. The acquired object data are evaluated in the control unit 30, wherein said acquired object data must satisfy all criteria within said control unit 30 for a checking of and/or confirmation of the preparation steps at the optical control panel 41. A control command for checking off and/or confirmation of the preparation steps is respectively associated with unique and selected gestures and/or movements of the operator 22 in connection with the optical control panel 41. A modified output information is subsequently output by the control unit 30 in method step 103 and output in method step 104.

Figure 8:
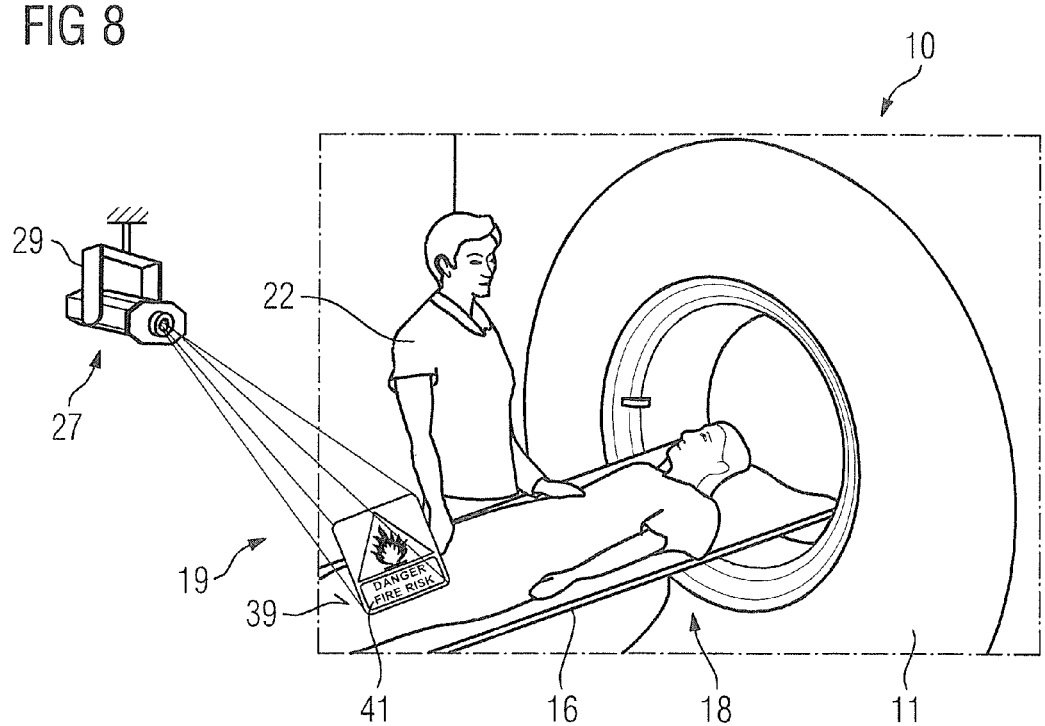
FIG. 8 shows an exemplary embodiment of a projection of a warning notification during a preparation of the patient for a medical imaging examination.

The optical output information is formed by a safety instruction in FIG. 8. The optical output information can also be formed by an optical control panel 41, wherein the response of the operator 22 can be formed by a confirmation of a recognition of the safety information. For example, this can take place by a gesture (as already described with regard to FIG. 3 through 6) and/or by means of an acoustic signal (for example by means of an acoustic speech input of the operator 22).

Alternatively or additionally, the operator 22 can make an input and/or a selection at the optical control panel 41 by means of an acoustic input, wherein here the acoustic object data acquisition unit 25 detects the acoustic input and/or selection in method step 100. The input and/or selection that is made by the operator 22 and detected by the acoustic object data acquisition unit 25 and/or the 3D image data acquisition unit is subsequently evaluated by the control unit 30 in method steps 102 and 103. Here as well, the control unit 30 subsequently generates a control command (for example a control command regarding a movement of the patient bearing device) and/or changes settings for the pending medical imaging examination depending on the input and/or selection of the operator 22. In addition to this, an additional output information is generated by the control unit 30 and output to the operator 22 by means of the projection unit and/or the acoustic output unit 28. The additional output information can include an additional optical control panel 41 and/or an acoustic output. Correction can be made by the operator 22 by means of the additional output information. The operator 22 thus can additionally be notified of changes.

The method according to the invention can be ended by a termination criterion, for example in that: the operator 22 makes a speech input; and/or the operator 22 leaves the examination room 19; and/or the medical imaging examination is ended; and/or additional termination criteria 106 that appear to be reasonable to those skilled in the art.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to communicate between a control processor of a medical imaging device and at least one of a patient on a patient support device from whom a medical image is to be obtained in a medical imaging examination, and an operator implementing said medical imaging examination, said control processor being located in a control room and said operator and said patient being located in an examination room that is outside of said control room, said method comprising:

with an object data detector located in the examination room, detecting object data of said operator;

automatically transferring the detected object data from the object data detector to said control processor;

in said control processor, automatically using said object data to determine determined information about said operator in said examination room;

in said control processor, automatically generating output information using said determined information; and from said control processor, presenting said output information at a presentation location within said examination room.

2. A method as claimed in claim 1 comprising determining said determined information of said operator from the group consisting of position information of said operator during the medical imaging examination and movement information of said operator during the medical imaging examination.

3. A method as claimed in claim 1 comprising generating said output information as output information selected from the group consisting of a safety instruction, and a specific instruction to the operator.

4. A method as claimed in claim 1 comprising generating said output information as a safety instruction selected from the group consisting of an instruction indicating an incorrect positioning of the patient on the patient support device, a safety instruction indicating a presence of an incorrect object on said patient support device, a safety instruction indicating a risk of harm to the patient during said medical imaging examination that arises due to preparation of the patient for said medical imaging examination, and a safety instruction indicating a risk to a component of said medical imaging device that arises due to preparation of the patient for said medical imaging examination.

5. A method as claimed in claim 1 comprising generating said output information as at least one image designed to reduce stress, or as an optical stimulus for the patient during said medical imaging examination.

6. A method as claimed in claim 1 comprising detecting said object data as optical 3D image data with a 3D image data detector as said object data detector.

7. A method as claimed in claim 1 comprising acquiring said object data as acoustic object data with an acoustic object data detector as said object data detector.

8. A method as claimed in claim 1 comprising generating said output information to include acoustic speech output information.

9. A method as claimed in claim 1 comprising:
generating said output information to include optical output information; and
projecting said optical output information at a presentation surface, as said presentation location.

10. A method as claimed in claim 9 comprising generating said optical output information with presentation color having a maximum contrast relative to said presentation surface.

11. A method as claimed in claim 9 comprising automatically selecting said presentation location for said presentation surface in said examination room dependent on a viewing direction of at least one of said operator and said patient.

12. A method as claimed in claim 9 comprising:
generating said optical output information to include medical image information stored in a database; and
projecting said medical image information onto the patient as said presentation surface.

13. A method as claimed in claim 9 comprising generating said optical output information to include an optical control panel.

14. A method as claimed in claim 13 comprising, in said control processor, automatically selecting at least one of a position of said optical control panel and a size of said optical control panel dependent on said object data of the operator detected by said object data detector.

15. A method as claimed in claim 13 comprising:
as part of said object data, detecting a gesture made by the operator in said examination room;

in said control processor, interpreting said gesture as operation of a slider of said optical control panel; and
from said control processor, automatically responding to the interpreted operation of said slider to set at least one of a scan region of the patient and a data acquisition region of said medical imaging device for said medical imaging examination.

16. A method as claimed in claim 1 comprising, after presenting said output information at said presentation location in said examination room, detecting, with said object data detector, a response of at least one of the operator and the patient to said output information.

17. A method as claimed in claim 16 comprising:
detecting said response from at least one of detected acoustic object data and detected optical object data; and
in said control processor, automatically interpreting said response as at least one of an input of a setting of said medical imaging device and a control command for operating said medical imaging device.

18. A method as claimed in claim 16 comprising, in said control processor, automatically determining additional output information from said response.

19. A method as claimed in claim 18 comprising generating said additional output information as a control command for operating said medical imaging device.

20. A method as claimed in claim 18 comprising:
generating said additional output information as an optical control panel; and
projecting said optical control panel onto a presentation surface in the examination room at said presentation location.

21. A method as claimed in claim 18 comprising presenting said additional output information in said examination room both acoustically and optically.

22. A method as claimed in claim 1 comprising:
detecting said object data as acoustic object data and as optical object data; and
detecting said acoustical object data and said optical object data simultaneously.

23. A method as claimed in claim 1, comprising:
with said object data detector, also detecting object data of said patient and automatically transferring the acquired object data of the patient from the object data detector to said control processor;
in said control processor, automatically using said object data of the patient to determine determined information about the patient in the examination room; and
in said control processor, generating said output information also using the determined information about said patient in said control room.

24. A method as claimed in claim 1 wherein said patient is situated on a patient support device in said examination room, and wherein said method comprises:
with said object data detector, also detecting object data of said patient support device and automatically transferring the detected object data of the patient support device to said control processor;
in said control processor, automatically using said object data of the patient support device to determine determined information about said patient support device in said examination room; and
in said control processor, automatically generating said output information also using said determined information about said patient support device in said examination room.

25. A medical imaging system as claimed in claim 1, comprising:

said object data detector being configured to also detect object data of said patient and to automatically transfer the acquired object data of the patient from the object data detector to said control processor;

said control processor being configured to automatically use said object data of the patient to determine determined information about the patient in the examination room; and said control processor being configured to generate said output information also using the determined information about said patient in said control room.

26. A medical imaging system as claimed in claim 1 wherein said patient is situated on a patient support device in said examination room, and wherein said method comprises:

said object data detector being configured to also detect object data of said patient support device and to automatically transfer the detected object data of the patient support device to said control processor;

said control processor being configured to automatically use said object data of the patient support device to determine determined information about said patient support device in said examination room; and said control processor being configured to automatically generate said output information also using said determined information about said patient support device in said examination room.

27. A medical imaging system to communicate between a control processor of a medical imaging device and at least one of a patient on a patient support device of whom a medical image is to be obtained in a medical imaging examination, and an operator implementing said medical imaging examination, said control processor being located in a control room and said operator and said patient being located in an examination room that is outside of said control room, said medical imaging system comprising:

an object data detector located in the examination room, that detects object data of said operator;

said object data detector being configured to automatically transfer the acquired object data from the object data detector to said control processor;

said control processor being configured to automatically determine determined information about said operator in said examination room;

said control processor, being configured to automatically generate output information using said determined information; and said control processing being configured to cause said output information to be presented at a presentation location within said examination room.

28. A medical imaging system as claimed in claim 27 wherein:

said control processor is configured to generate said output information as an optical control panel; and said is medical imaging system comprises a projector in communication with said control processor configured to project said optical control panel at said presentation location, selected from the group consisting of an external housing of said medical imaging device, said patient support device, and said patient.

29. A medical imaging system as claimed in claim 28 wherein:

said object data detector is a 3D image data detector that detects, as said object data, a gesture made by at least one of the operator or the patient with respect to said control panel; and said control processor is configured to interpret said gesture as at least one of a control command for operating said medical imaging device in said medical imaging examination and a setting input to said medical imaging device for said medical imaging examination.

30. A medical imaging system as claimed in claim 28 comprising a positioning unit configured to adjust or align a spatial position of said projector in said examination room.

31. A medical imaging system as claimed in claim 27 wherein said object data detector is a 3D image data detector, and wherein said medical imaging system comprises at least one positioning unit that adjusts or aligns a spatial orientation of said 3D data acquisition unit in said examination room.

32. A medical imaging system as claimed in claim 31 wherein said positioning unit is located in said control room.

33. A medical imaging system as claimed in claim 31 wherein:

said control processor is configured to generate said output information as an optical control panel;

said medical imaging system comprises a projector in communication with said control computer configured to project said optical control panel at said presentation location; and said 3D image data acquisition unit has an optical axis;

said projector has an optical axis; and said positioning unit is configured to selectively orient said optical axis of the 3D image acquisition unit with respect to said optical axis of said projector.

34. A medical imaging system as claimed in claim 33 wherein at least one of said projector and said 3D image data acquisition unit are mounted on a wall of said examination room.

35. A medical imaging system as claimed in claim 27 wherein said object data detector is in acoustic object data detector that detects acoustic object data originating from the operator.

36. A medical imaging system as claimed in claim 27 wherein said control processor is configured to generate said output information as at least one acoustic signal.

37. A medical imaging system as claimed in claim 36 comprising an acoustic output unit in communication with said control processor that emits said at least one acoustic signal into said examination room.

* * * * *